(12) United States Patent
Schoolcraft et al.

(10) Patent No.: US 9,874,572 B2
(45) Date of Patent: Jan. 23, 2018

(54) SECRETOME PROFILE-FACILITATED IN VITRO FERTILIZATION

(71) Applicant: FERTILITY LAB SCIENCES, LLC, Englewood, CO (US)

(72) Inventors: William B. Schoolcraft, Englewood, CO (US); Mandy Katz-Jaffe, Denver, CO (US); Susanna McReynolds, Parker, CO (US)

(73) Assignee: FERTILITY LAB SCIENCES, LLC, Englewood, CO (US)

( * ) Notice: Subject to any disclaimer, the term of this patent is extended or adjusted under 35 U.S.C. 154(b) by 0 days.

(21) Appl. No.: 15/648,296

(22) Filed: Jul. 12, 2017

(65) Prior Publication Data

US 2017/0328913 A1 Nov. 16, 2017

Related U.S. Application Data

(60) Division of application No. 15/052,475, filed on Feb. 24, 2016, now Pat. No. 9,714,950, which is a continuation of application No. 13/081,463, filed on Apr. 6, 2011, now abandoned.

(60) Provisional application No. 61/321,448, filed on Apr. 6, 2010.

(51) Int. Cl.
*G01N 33/00* (2006.01)
*G01N 33/68* (2006.01)
*G01N 33/543* (2006.01)

(52) U.S. Cl.
CPC ......... *G01N 33/689* (2013.01); *G01N 33/543* (2013.01); *G01N 2800/52* (2013.01)

(58) Field of Classification Search
CPC .................. G01N 33/689; G01N 33/543
See application file for complete search history.

(56) References Cited

U.S. PATENT DOCUMENTS

| | | | |
|---|---|---|---|
| 9,714,950 B2 * | 7/2017 | Schoolcraft | G01N 33/689 |
| 2004/0005563 A1 | 1/2004 | Mack et al. | |
| 2004/0181344 A1 | 9/2004 | Stephanopoulos et al. | |
| 2007/0161125 A1 * | 7/2007 | Rosenfeld | G01N 33/689 436/518 |
| 2009/0305242 A1 | 10/2009 | Miyata et al. | |

FOREIGN PATENT DOCUMENTS

| | | |
|---|---|---|
| EP | 1847595 A1 | 10/2007 |
| WO | 2009075862 A1 | 6/2009 |
| WO | 2009143519 A2 | 11/2009 |

OTHER PUBLICATIONS

Kuwbara et al., (JBC. Feb. 1, 2002; 277(5):3487-3497).*
Saussez et al., (Annals of Surgical Oncology. 2006;13(7):999-1009).*
Dominguez et al., (Human Reproduction. 2008; 23(9):1993-2000).*
Wang et al., (J Biomed Res. Jan. 2011;25(1):63-70).*
Zhu et al., (J Proteome Res. Aug. 2009;8(8):3969-76).*
Moisan et al.,(Leukemia. 2003;17:751-759).*

(Continued)

*Primary Examiner* — Cherie M Stanfield
(74) *Attorney, Agent, or Firm* — Brownstein Hyatt Farber Schreck LLP; Cara L. Crowley-Weber

(57) ABSTRACT

Secretome profiling improves the pregnancy success rate of in vitro fertilization processes, while reducing the risk of multiple births.

5 Claims, 4 Drawing Sheets

(56) References Cited

OTHER PUBLICATIONS

Cao et al., (Invest Opthalmol Vis Sci. Sep. 2002;43(9)2897-904).*
Lohr (Folia Biol (Praha). 2007;53(4)1 09-28).*
Abate et al. (2002) "Sex Steroid Hormones, Upper Body Obesity, and Insulin Resistance," J. of Clinical Endocrinology & Metabolism, 87(10):4522-4527.
Affymetrix U95Av2 Genechip Information from www.affymetrix.com/catalog/131538/AFFY/Human+Genome+U95+Set. Last accessed Mar. 20, 2017 (18 pages).
Cao et al. (2002) "Detection of differentially expressed genes in healing mouse corneas, using cDNA microarrays," Invest. Opthalmol. Vis. Sci., 43(9)1897-2904.
Chen et al. (2006) "Transcriptome analysis in blastocyst hatching by cDNA microarray," Human Reproduction, 20 (9):2492-2501.
Combelles and Racowsky (2006) "Protein expression profiles of early embryos—an important step in the right direction: just not quite ready for prime time," Fertility and Sterility, 86(2):493-494.
Cui (2011) "An integrated transcriptomic and computational analysis for biomarker identification in gastric cancer," Nucleic Acids Res., 39(4):1197-1207; ePub Oct. 21, 2010.
Dominguez et al. (2008) "Comparative protein-profile analysis of implanted versus non-implanted human blastocysts," Human Reproduction, 23(9):1993-2000.
ELISA article downloaded Apr. 6, 2011 from the website bio.davidson.edu/courses/genomics/method/ELISA.html.
Harn et al., Article downloaded from ovidsp.tx.ovid.com/sp-3.8.1a/ovidweb.cgi; 5 pages.
Herr et al. (2011) "Potential Biomarkers of Temporomandibular Joint Disorders," J. of Oral and Maxillofacial Surgery, 69.1:41-47.
Katz-Jaffe et al. (2005) "A proteomic analysis of mammalian preimplantation embryonic development," Reproduction, 130:899-905.
Katz-Jaffe et al. (2006) "Proteomic analysis of individual human embryos to identify novel biomarkers of development and viability," Fertility and Sterility, 85(1):101-107.
Katz-Jaffe et al. (2006) "Analysis of protein expression (secretome) by human and mouse preimplantation embryos," Fertility and Sterility, (2006) 86:678-685.
Katz-Jaffe et al. (2007) "Embryology in the era of proteomics," Theriogenology, 68S:S125-S130.
Katz-Jaffe et al. (2009) "The role of proteomics in defining the human embryonic secretome," Molecular Human Reproduction, 15(5):271-277.
Katz-Jaffe et al. (2013) "Embryology in the era of proteomics," Fertility & Sterility, 99(4):1073-1077.
Kim et al. (2009) "Tumor Self-Seeding by Circulating Cancer Cells," Cell, 139(7):1315-1326.
Kuwbara et al. (2002) "Galectin-7 (PIG 1) Exhibits Pro-Apoptotic Function through JNK Activation and Mitochondrial Cytochrome c Release," J. of Biol. Chem., 277(5):3487-3497.
Lohr et al. (2007) "Murine Homodimeric Adhesion/Growth-Regulatory Galectins-1, -2 and -7: Comparative Profiling of Gene/Promoter Sequences by Database Mining, of Expression by RT-PCR/Immunohistochemistry and of Contact Sites for Carbohydrate Ligands by Computational Chemistry," Folia Biol. (Praha), 53(4):109-128.
Majore et al. (2011) "Growth and Differentiation Properties of Mesenchymal Stromal Cell Populations Derived from Whole Human Umbilical Cord," Stem Cell Rev., 7(1):17-31.
Moisan et al. (2003) "Upregulation of galectin-7 in murine lymphoma cells is associated with progression toward an aggressive phenotype," Leukemia, 17:751-759.
RayBiotech, Inc. (2017) "Documentation of various commercial Cytokine Arrays contining galectin-7" from www.raybiotech.com. Last accessed Mar. 22, 2017 (35 pages).
Saussez et al. (2006) "Galectin 7 (p53-Induced Gene 1): A New Prognostic Predictor of Recurrence and Survival in Stage IV Hypopharyngeal Cancer," Annals of Surgical Oncology, 13(7): 999-1009.
Saw et al. (2011) "Profibrotic Phenotype of Conjunctival Fibroblasts from Mucous Membrane Pemphigoid," Am. J. Path., 178(1):187-197.
Wang et al. (2011) "Development and optimization of an antibody array method for potential cancer biomarker detection," J. of Bio. Research, 25(1):63-70.
Zhu et al. (2009) "Profiling protein markers associated with the sensitivity to concurrent chemoradiotherapy in Human cervical carcinoma," J. of Proteome Res., 8(8):3969-3676.
International Search Report & Written Opinion for PCT/US2011/031474 dated Feb. 17, 2012.
communication pursuant to Article 94(3) EPC dated Dec. 7, 2016.
First Examination Report dated Feb. 20, 2017.

* cited by examiner

CCRM Donor Oocyte Cycles
(n=1063)

| | |
|---|---|
| Average Age of Oocyte Donor | 26.6yrs |
| Average Age of Recipient Uterus | 40.6yrs |
| Average # Oocytes Retrieved | 21.26 |
| Average % Blastocyst Development | 65% |
| Average # Embryos Transferred | 2.0 |
| Average # Embryos Cryopreserved | 4.8 |
| Biochemical Pregnancy | 90.9% |
| Clinical Pregnancy Rate (FHT) | 84.6% |
| Implantation Rate (FHT) | 66.6% |

*FIG. 2*

SECRETOME PROFILE-FACILITATED IN VITRO FERTILIZATION

RELATED APPLICATIONS

This application is a divisional of U.S. application Ser. No. 15/052,475, filed Feb. 24, 2016, issued on Jul. 25, 2017 as U.S. Pat. No. 9,714,950, which is a continuation of U.S. application Ser. No. 13/081,463, filed Apr. 6, 2011, which claims benefit of priority to U.S. Provisional Patent Application No. 61/321,448 filed Apr. 6, 2010, each of which is incorporated by reference to the same extent as though fully replicated herein.

SEQUENCE LISTING

This application includes a Sequence Listing, as set forth in an ASCII-compliant text file named "CCRMProtein_ST25.txt", created on Apr. 6, 2011, and containing 2263 kilobytes, which is incorporated by reference to the same extent as though fully replicated herein.

BACKGROUND

Field

The invention relates to the field of in vitro fertilization (IVF), which is a process by which mammalian egg cells are fertilized by sperm outside the womb. More particularly, evaluation of a secretome profile is used to enhance the pregnancy success rate when the fertilized egg is implanted into a patient's uterus.

Description of the Related Art

IVF infertility treatment offers infertile couples a chance to have a biologically related child. IVF may overcome female infertility due to problems of the fallopian tube or endometriosis. IVF also overcomes male infertility due to problems with sperm quality or quantity. The IVF process involves hormonally controlling the ovulatory process, removing eggs (termed ova) from the woman's ovaries and permitting the sperm to fertilize the eggs in a fluid medium. The fertilized egg, termed an embryo, is subsequently transferred to the patient's uterus with the intent of establishing a successful pregnancy. Due to expensive procedural costs, IVF is only attempted after the failure of less expensive fertility treatments.

FIG. 1 displays a schematic for mammalian blastocyst implantation. Mammalian embryo implantation is a complex and intricate process involving numerous biological changes at both the embryo and endometrial level. The interaction between the blastocyst and the endometrium is a function of both a receptive endometrial environment and a healthy blastocyst. A blastocyst failing to implant or an endometrium failing to sustain growth and differentiation will result in spontaneous abortion. The prior art teaches very little about the embryo's role in the events leading to the attachment of a viable blastocyst to a receptive uterine luminal epithelium.

IVF treatment begins with administration of hormonal medications to stimulate ovarian follicle production, such as gonadotropins hormones. The prevention of spontaneous ovulation involves using other hormones, such as GnRH antagonists or GnRH agonists that block the natural surge of luteinizing hormone. With adequate follicular maturation, administration of human chorionic gonadotropin hormone causes ovulation approximately 42 hours after the administration. However, the egg retrieval procedure takes place just prior to ovulation, in order to recover the eggs from the ovary. The egg retrieval proceeds using a transvaginal technique involving an ultrasound-guided needle that pierces the vaginal wall to reach the ovaries. After recovery of the follicles through the needle, the follicular fluid is provided to the IVF laboratory to identify eggs. Typically, the procedure retrieves between 10 and 30 eggs. The retrieval procedure takes approximately 20 minutes and is usually done under conscious sedation or general anesthesia.

For IVF, the fertilization of the egg (termed insemination) proceeds in the laboratory where the identified eggs and semen are usually incubated together in a culture media. The confirmation of fertilization proceeds by monitoring the eggs for cell division. For instance, a fertilized egg may show two pronuclei. In certain situations, such as low sperm count or motility, a single sperm may be injected directly into the egg using a method called intracytoplasmic sperm injection (ICSI). In another option known as gamete intrafallopian transfer, eggs are removed from the woman and placed in one of the fallopian tubes, along with the man's sperm. In this example, fertilization occurs within the women's body, a process termed in vivo fertilization.

Selected embryos are transferred to the patient's uterus through a thin, plastic catheter, which goes through the vagina and cervix. Typically, transfer of 6-8 cell stage embryos to the uterus occurs three days after embryo retrieval. Alternatively, embryos can be placed into an extended culture system with a transfer done at the blastocyst stage at approximately five days post-retrieval. Blastocyst stage transfers often result in higher pregnancy rates. Additionally, embryonic cryopreservation, or the storage of embryos in a frozen state, is feasible until uterine transfer. For example, the first term pregnancy derived from a frozen human embryo was reported in 1984.

Despite progressively improving IVF pregnancy rates, the majority of transferred human embryos result in implantation failure. For example, Canadian clinics reported an average pregnancy rate of 35% for one cycle, but a live birth rate of only 27% in 2006. Moreover, implantation success rates may decrease with the increasing maternal age, if donor eggs are not used. Various factors are associated with implantation failure, including embryo chromosome aneuploidies related to advanced maternal age and maternal factors such as endometrium response failure to hormone regulation.

To overcome low implantation success rate, multiple embryos are commonly transferred during a single IVF procedure. The process for selecting embryos for transfer often involves grading methods developed in individual laboratories to judge oocyte and embryo quality. An arbitrary embryo score, involving the number and quality of embryos, may reveal the probability of pregnancy success post-transfer. For example, an embryologist may grade embryos using morphological qualities including the number of cells, clearness of cytoplasm, evenness of growth and degree of fragmentation. However, embryo selection based on morphological qualities is not precise. Often, several embryos selected for these general qualities are implanted to improve the chance of pregnancy. The number of embryos transferred depends upon the number available, the age of the woman and other health and diagnostic factors.

The transfer of multiple embryos, however, often results in multiple pregnancies, a major complication of IVF. In general, multiple pregnancies, specifically, more than twins, hold maternal and fetal risks. For example, multiple births are associated with increased risk of pregnancy loss, neonatal morbidity, obstetrical complications, and prematurity with potential for long term damage. Some countries implemented strict limits on the number of transferred embryos to reduce the risk of high-order multiples (e.g., triplets or more). However, these limitations are not universally followed or accepted.

SUMMARY

In one embodiment, a system for enhancing the pregnancy success rate of in vitro fertilization includes a means for determining the secretome profile of an embryo to identify proteins, polypeptides, oligopeptides or protein fragments implicated in implantation success and a means for recommending whether to implant the embryo, such as a blastocyst, on the basis of the secretome profile.

The CDC data from 2006 shows that use of donor eggs in a 40 year old woman will result in a live birth 54% of the time. This compares to 20.6% using the woman's own eggs. Thus, an opportunity exists for the instrumentalities of this disclosure to facilitate success rates approximating the use of donor eggs when using one's own eggs, and may even permit higher success rates due to better selection of viable embryos.

In an embodiment, a system is provided for enhancing the pregnancy success rate of in vitro fertilization. The system includes an electronic system to configured to gather secretome data as a secretome profile of an embryo by quantitating proteins implicated in implantation success. A model is provided for use in recommending whether to implant the embryo on the basis of this secretome profile. The secretome date may be, for example, provided by use of mass spectroscopy or ELISA measurements.

According to one aspect of the system, the secretome profile may be provided by using proteins as embryo secretions in culture media that may be linked to changed odds of implantation success, for example, as may be found in one or more sequences found in SEQID Nos. 1-404. The sequences of SEQID Nos. 261-404 are preferred for this use. Particularly preferred are the sequences of SEQID Nos. 310, 311, 313, 317, 318, 319, 334, 335, 336, 337, 338, 339, 340, 341, 342, 343, 345, 346, 347, 348, 349, 350, 368, 371, 374, 383, 391, 397, 398, 399, 402, 403, and 404. The sequences of SEQID Nos. 310, 311, 313, 318, 319, 334, 335, 336, 337, 338, 339, 340, 341, 342, 343, 345, 346, 347, 348, 349, 350, 368, 371, 374, 391, 397, 398, 399, 402, 403, and 404 are associated with increased odds of implantation success, whereas those of SEQID Nos. 317 and 383 are associated with failure or aneuploidy.

In an embodiment, a method of in vitro fertilization entails determining the secretome profile of a candidate embryo by use of these sequences to ascertain proteins implicated in implantation success. This provides data that may be submitted to a model that associates one or more of these proteins with changes odds of implantation success or failure. A recommendation for implantation of the embryo may then be provided based upon the modeling outcome. The embryo may be conditionally implanted on the basis of the recommendation.

In an embodiment, there is an improved ELISA assay kit with a plurality of microwells for the quantitation of protein content in a sample. The microwells are constructed and arranged to quantitate for a plurality of proteins selected from these sequences.

BRIEF DESCRIPTION OF THE FIGURES

FIG. 2 is a table that illustrates the success rates from donor oocyte IVF cycles.

DETAILED DESCRIPTION

Figure 1:
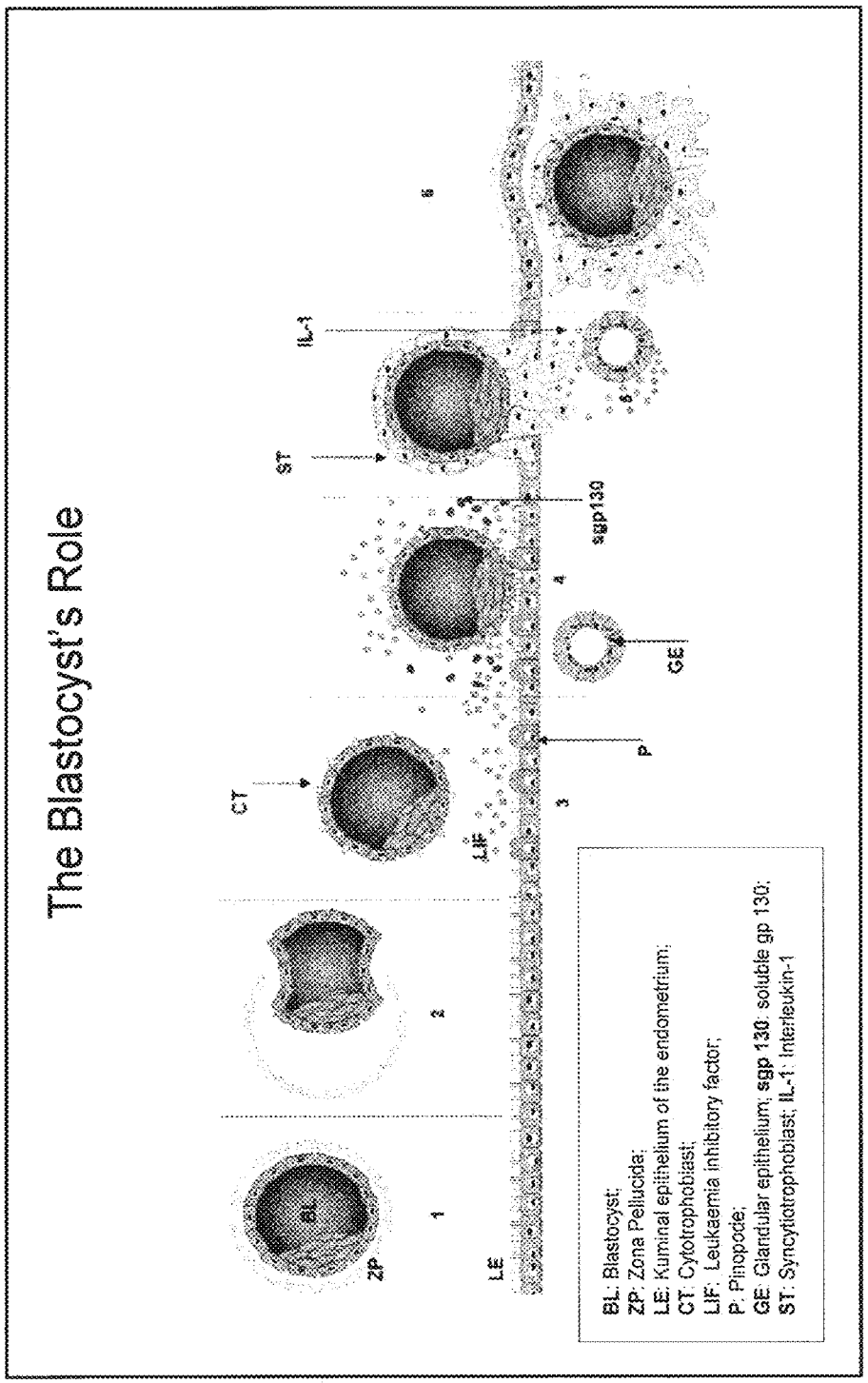
FIG. 1 is a diagram illustrating the process blastocyst implantation.

The following definitions are provided to facilitate understanding of certain terms used herein and are not meant to limit the scope of the present disclosure.

The term "secretome panel" refers to a collection of individual proteins, polypeptides, oligopeptides or protein fragments that are differentially expressed and secreted by an embryo. The proteins, polypeptides, oligopeptides or protein fragments of the secretome panel are selected based on predictions of developmental competence and implantation potential of an embryo.

The term "spent media" refers to media surrounding an embryo that accumulates proteins secreted from the embryo.

The term "secretome profiling" refers to qualitative and quantitative analysis of a secretome panel collected from spent media.

There will now be shown and described a system for enhancing the pregnancy success rate of in vitro fertilization involving non-invasive secretome profiling of an embryo. Secretome profiling may be performed on embryos at differing embryonic developmental stages, such as day one through day six embryos.

Non-limiting examples of proteins comprising the secretome panel include proteins involved in amino acid metabolism, lipid metabolism, carbohydrate metabolism, signal transduction, apoptosis, transcription and combinations thereof. In one example, an embryo secretes a protein that is involved in amino acid metabolism, thereby indicating potential for successful embryo implantation. In another example, an embryo secretes a protein that is involved in apoptosis, thereby indicating a reduced potential for successful blastocyst implantation. Nonlimiting examples of the number of proteins comprising the secretome panel includes ≥250 proteins, ≥100 proteins, ≥50 proteins, ≥20 proteins or ≥10 proteins.

Secretome profiling involves assessment of a secretome panel. Secretome profiling is a noninvasive method for predicting developmental competence and viability of an embryo. Comparison of secretome profiles between developing embryos and degenerating embryos, both at the same developmental stage, reveals significant differences in protein expression. Moreover, secretome profiling provides a molecular perspective of the functioning biochemical pathways present during embryo development. A noninvasive secretome profiling assay correlates embryonic secretome to embryonic viability, thereby facilitating single embryo transfer during in vitro fertilization.

FIG. 2 highlights the importance of embryo developmental competence by showing high success rates from donor oocyte IVF cycles using young reproductive age oocytes transferred to an advanced maternal age endometrium. The data is provided for a Colorado clinic from 2004-2009 including outcomes for over 1000 donor oocyte cycles. These results demonstrate a 66.6% implantation rate for IVF recipients with an average endometrial age of 40.6 years and donor oocytes with an average age of 26.6 years.

In one embodiment, secretome profiling occurs by assessing a secretome panel via Enzyme-Linked Immunosorbent Assay (ELISA). In another embodiment, secretome profiling proceeds by assessing a secretome panel via mass spectrometry.

Non-limiting examples of solid-state substrates used in ELISA include microwell plates, such as 96-well plates, 384-well plates and 8-well strips, microarray slides and nitrocellulose membranes. In one embodiment, glass microarray surfaces contain chemical functional groups such as epoxy, amine or aldehyde. In one embodiment, microwell plate material comprises polystyrene.

The term "capture antibody" refers to an antibody secured, either covalently or non-covalently, to a solid-state substrate. The capture antibody recognizes and binds to a specific antigen such as a protein, a polypeptide, an oligopeptide, a protein fragment, a carbohydrate or a small molecule. In one example, a solid-state substrate is functionalized with capture antibodies by passive adsorption or by specific binding. For example, specific binding of capture antibodies may occur using biotinylated capture antibodies and streptavidin-coated solid-state substrates. In another example, solid-state substrates are functionalized with antigens via passive adsorption.

Non-limiting examples of ELISA types include direct, indirect, competitive, and sandwich. In one example, proteins from the secretome panel are detected on a solid-state substrate using either a primary labeled antibody or a secondary labeled antibody. In another example, proteins from the secretome panels are detecting using a sandwich ELISA wherein a protein from the secretome panel is bound between two primary antibodies, namely the capture antibody and the detection antibody. Non-limiting examples of antibody labels include enzymes and fluororphores. In one embodiment, an enzyme that is conjugated to a detection antibody binds to a substrate producing either a chromogenic, fluorescent or chemiluminescent signal that is proportional to the quantity of protein from the secretome panel.

Figure 3:
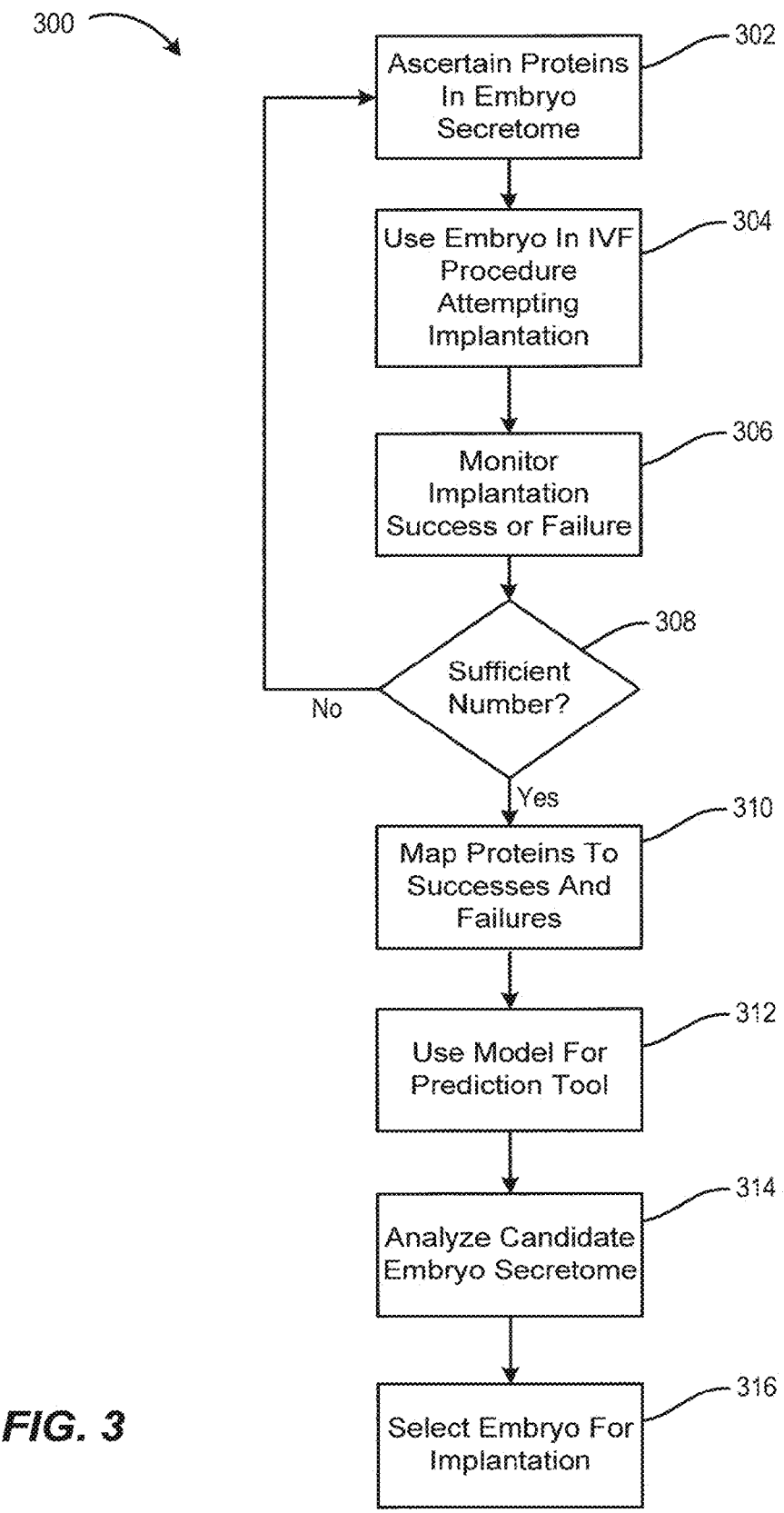
FIG. 3 is a flow chart for a method of developing and using a predictive model that may be used to assess embryo viability as a candidate for use in an IVF implantation procedure.

FIG. 3 shows a method 300 implementing the concepts described above to identify those embryos having the greatest chanced for implantation success rates. Step 302 entails ascertaining the secretome of proteins secreted into culture medium by an egg, blastocyst or developing embryo (hereinafter "embryo") that has been previously fertilized by methods known to the art. Step 302 may be performed at any time, including before an egg is fertilized or immediately thereafter. More typical times to sample the media include form one to five days after fertilization occurs. Step 302 is preferably conducted before step 304, but samples of the culture medium may be frozen for later analysis. The embryo is then used 304 in an IVF procedure attempting to implant the embryo in a woman who desires to have a baby. The implantation successes and failures are monitored 306 to collect data relating the successes and failures to one or more proteins of the secretome. Once a sufficient number of instances have transpired 308 to provide for statistical significance, the proteins are mapped 310 to the instances of success and failure. The exact manner of mapping is not of particular importance, as there a number of biostatistical analysis software products are commercially available. For example, this may be done using the JMP® 9 packages from SAS of Cary, N.C. to implement methods as taught by Zar, Biostatistical Analysis, 5th Ed., Prentice Hall (2007) to map the secretome profiles using also time as a variable. The mapping may be multivariate, or by an artificially intelligent algorithm, such as a neural network. This model may be then used 312 as a predictive tool to select embryos for implantation based upon their secretome profile. This is done by analyzing 314 the secretome of candidate embryos for implantation with use of the model to predict implantation success or failure. One or more of the selected embryos are then implanted 316

Figure 4:
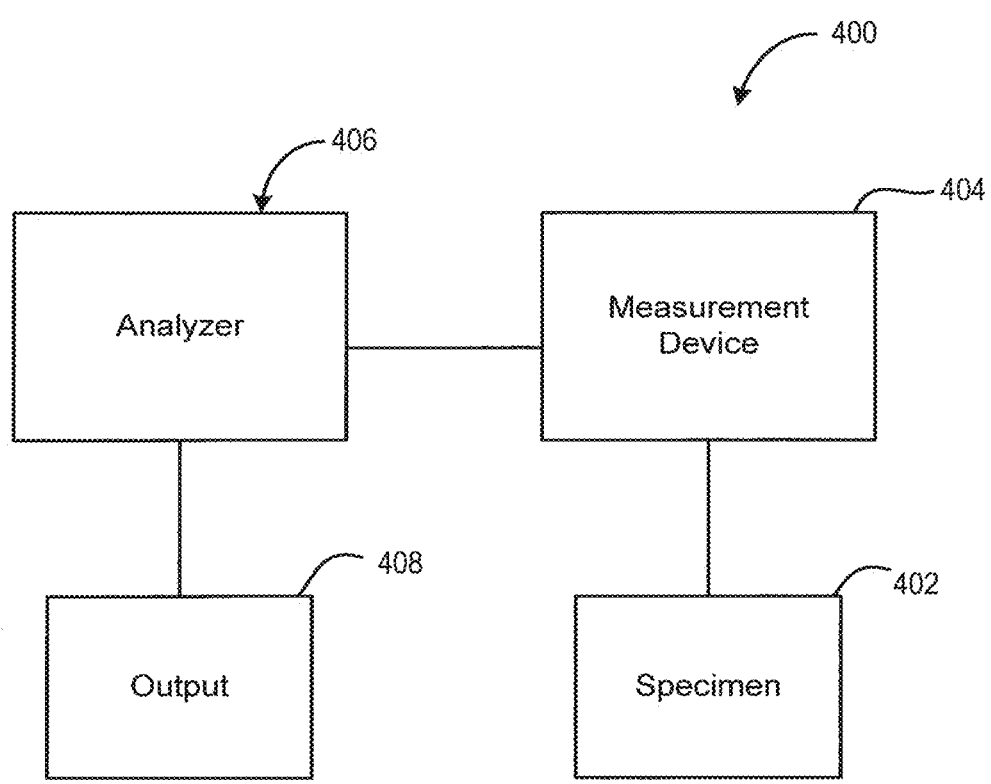
FIG. 4 shows a system that analyzes the secretome of an embryo to assess viability.

FIG. 4 shows an analytical system 400 that may be used in step 314 according to one embodiment. A specimen 402 contains a sample of culture medium that is collected for secretome analysis as described above. By way of example, this specimen may contain culture medium in the form of a single or multi-well ELISA assay, or in a form that has been pre-processed for mass spectroscopy analysis. A corresponding measurement device 404 obtains primary measurements from the specimen 402. The measurements are representative of one or more proteins in the secretome that have been mapped to incidences of implantation success of failure. The model for this mapping is provided in step 312 of method 300 and resides on analyzer 406, which may be a computer operating on program instructions. The analyzer 406 receives signals from the measurement device 404 and interprets these by computational analysis according to the model then provides the results of computational analysis to an output device 408, which may be printer or an optical display. The various components of system 400 may be partially integrated, such as by combining the measurement device 404, analyzer 406, and output device 408 into one integrated system.

It will be appreciated that perceptive use of the instrumentalities described herein may result in a better selection of healthy embryos, such as blastocysts, for implantation. Thus, fewer blastocysts need to be implemented, such that there is lower risk of multiple pregnancies while achieving a higher overall pregnancy success rate.

The following descriptions will show and describe, by way of non-limiting examples, a process for improving pregnancy success rates with lower incidence of multiple births. The following examples describe secretome profiling of spent media from human blastocysts to provide implantation recommendation. It is to be understood that these examples are provided by way of illustration and should not be unduly construed to limit the scope of what is disclosed herein.

Example 1

Secretome Profiling of Human Embryos Using Mass Spectrometry

The following nonlimiting example teaches by way of illustration, not by limitation, secretome profiling of a human embryo using mass spectrometry (MS). Human cleavage-stage embryos were cultured in 10 μL drops of G1 supplemented with 2.5 mg/mL recombinant albumin under oil at 37° C., 6% $CO_2$, 5% $O_2$ for 24 hours. The embryos were washed twice in G2 culture media and further cultured in 10 μL drops of G2 supplemented with 2.5 mg/mL recombinant albumin under oil at 37° C., 6% $CO_2$, 5% $O_2$ for 48 hours with a fresh drop of G2 media added after 24 hours. Spent media samples of blastocysts were transferred into 0.65 mL Eppendorf tubes. Control groups comprised media cultured and collected under the same conditions but without embryos.

Micro-drops of spent media were depleted of human serum albumin (HSA) using Cibracron Blue Activated SwellGel Discs (Themo Fisher Scientific, Rockford, Ill.). The proteins in the spent media were separated by 1D gel electrophoresis (Invitrogen, Carlsbad, Calif.), followed by Coomassie staining. Twenty five individual bands were cut out from each sample lane and a standard in-gel digestion protocol was used based on previously used methods ((1.) Rosenfeld, J., Capdevielle, J., Guillemot, J. C. & Ferrara, P. In-gel digestion of proteins for internal sequence analysis after one- or two-dimensional gel electrophoresis. Anal. Biochem. 203, 173-179 (1992), (2.) Hellman, U., Wernstedt, C., Gonez, J. & Heldin, C. H. Improvement of an "In-Gel" digestion procedure for the micropreparation of internal protein fragments for amino acid sequencing. Anal. Biochem. 224, 451-455 (1995)). Iodoacteamide (IAM) was used for cysteine alkylation. The samples were analyzed on a LTQ-FT Ultra Hybrid Mass Spectrometer (Thermo/Finnigan; Waltham, Mass.) with a method based on a previously described protocol from Hansen et al., (Hansen KC, Kiemele L, Mailer O, O'Brien J, Shankar A, Fornetti J, Schedin P. An in-solution ultrasonication-assisted digestion method for improved extracellular matrix proteome coverage. Mol Cell Proteomics. 8(7):1648-57 (2009)).

Spent media samples were analyzed on a LTQ-FT Ultra Hybrid Mass Spectrometer (Thermo/Finnigan; Waltham, Mass.). Peptide desalting and separation was achieved using a dual capillary/nano pump HPLC system (Agilent 1200, Palo Alto, Calif.). On this system 8 µL of spent media sample was loaded onto a trapping column (ZORBAX 300SB-C18, dimensions 5×0.3 mm 5 um) and washed with 5% acetonitrile (ACN), 0.1% formic acid (FA) at a flow rate of 15 µL/min for 5 minutes. At this time, the trapping column was put online with the nano-pump at a flow rate of 350 nL/min. An 85 minute gradient, from 8% ACN to 40% ACN, was used to separate the peptides. The column was made from an in-house pulled 360/100 nm (outer/inner diameter) fused silica capillary packed with Jupiter C18 resin (Penomenex; Torrance, Calif.). The column was kept at a constant 40° C. using an in-house built column heater. Data acquisition was performed using the instrument supplied Xcalibur (version 2.0.6) software. The LC runs were monitored in positive ion mode by sequentially recording survey MS scans (m/z 400-2000), in the ICR cell, while three $MS^2$ were obtained in the ion trap via CID for the most intense ions. After two acquisitions of a given ion within 45 seconds, the ion was excluded for 150 seconds.

For data analysis, The Raw Distiller program (UCSF) was used to create a de-isotoped centroided peak lists from the raw spectra into the mascot format using the default settings. The peak lists were searched against the SwissProt Human database (51.6, *Homo sapiens* 15720 sequences) using Mascot™ server (Version 2.2, Matrix Science, Boston, Mass.). The search parameters are the same as those followed in Hansen et al., (Hansen K C, Kiemele L, Maller O, O'Brien J, Shankar A, Fornetti J, Schedin P. An in-solution ultrasonication-assisted digestion method for improved extracellular matrix proteome coverage. Mol Cell Proteomic. 8(7): 1648-57 (2009)). The Mascot results were loaded into Scaffold (v 2.06) and the runs were compared.

In one embodiment, MS analysis of spent media reveals a secretome panel of 261 individual proteins (Table 1). In one example, secretome profiling using the secretome panel of 261 proteins (Table 1), as analyzed by MS, identifies the potential for developmental competence and implantation success of a human embryo.

In one embodiment, analysis of spent media via MS reveals a secretome panel of 37 individual proteins (Table 2). Secretome profiling via MS of 37 individual proteins (Table 2) from spent media of human embryos correlates with embryonic viability and euploidy. The term "euploidy" refers to having a chromosome number that is an exact multiple of the haploid number for a human embryo, namely 23 pairs of chromosomes.

In Tables 1 and 2 below, the entries for "Entry Name" and ""Accession Number" refer to identifiers for published sequence data that is stored in bioinformatic databases including the Uniprot Knowledgebase, Swiss-Prot and TrEMBL. The information is made freely available to the world and is coordinated by the Swiss Institute of Bioinformatics, which is centrally administered in Lausanne, Switzerland with offices in Bern, Geneva and Zurich. The sequence information represented by these identifiers together with the representative publications is hereby incorporated by reference to the same extent as though fully replicated herein. For those proteins having isoforms, the sequences for Table 1 include consensus sequences for the primary isoforms, while sequences for Table 2 include also all other isoforms available at the time of filing.

TABLE 1

Proteins identified in spent media of human embryos.

| SEQ ID NO. | Protein Name | Entry Name | Protein Molecular Weight | Accession Number | Taxonomy |
|---|---|---|---|---|---|
| 1 | Serum albumin | ALBU_HUMAN | 69 kDa | P02768 | *Homo sapiens* |
| 2 | Serotransferrin | TRFE_HUMAN | 77 kDa | P02787 | *Homo sapiens* |
| 3 | Haptoglobin | HPT_HUMAN | 45 kDa | P00738 | *Homo sapiens* |
| 4 | Alpha-1-antitrypsin | A1AT_HUMAN | 47 kDa | P01009 | *Homo sapiens* |
| 5 | Alpha-2-macroglobulin | A2MG_HUMAN | 163 kDa | P01023 | *Homo sapiens* |
| 6 | Hemopexin | HEMO_HUMAN | 52 kDa | P02790 | *Homo sapiens* |
| 7 | Apolipoprotein A-I | APOA1_HUMAN | 31 kDa | P02647 | *Homo sapiens* |
| 8 | Ceruloplasmin | CERU_HUMAN | 122 kDa | P00450 | *Homo sapiens* |
| 9 | Vitamin D-binding protein | VTDB_HUMAN | 53 kDa | P02774 | *Homo sapiens* |
| 10 | Alpha-1-antichymotrypsin | AACT_HUMAN | 48 kDa | P01011 | *Homo sapiens* |
| 11 | Plasma protease C1 inhibitor | IC1_HUMAN | 55 kDa | P05155 | *Homo sapiens* |
| 12 | Alpha-1B-glycoprotein | A1BG_HUMAN | 54 kDa | P04217 | *Homo sapiens* |
| 13 | Hemoglobin subunit beta | HBB_HUMAN | 16 kDa | P68871 | *Homo sapiens* |
| 14 | Antithrombin-III | ANT3_HUMAN | 53 kDa | P01008 | *Homo sapiens* |
| 15 | Afamin | AFAM_HUMAN | 69 kDa | P43652 | *Homo sapiens* |
| 16 | Angiotensinogen | ANGT_HUMAN | 53 kDa | P01019 | *Homo sapiens* |
| 17 | Transthyretin | TTHY_HUMAN | 16 kDa | P02766 | *Homo sapiens* |
| 18 | Inter-alpha-trypsin inhibitor heavy chain H4 | ITIH4_HUMAN | 103 kDa | Q14624 | *Homo sapiens* |
| 19 | Complement factor B | CFAB_HUMAN | 86 kDa | P00751 | *Homo sapiens* |
| 20 | Hemoglobin subunit alpha | HBA_HUMAN | 15 kDa | P69905 | *Homo sapiens* |

TABLE 1-continued

Proteins identified in spent media of human embryos.

| SEQ ID NO. | Protein Name | Entry Name | Protein Molecular Weight | Accession Number | Taxonomy |
|---|---|---|---|---|---|
| 21 | Ig alpha-1 chain C region | IGHA1_HUMAN | 38 kDa | P01876 | *Homo sapiens* |
| 22 | Ig gamma-1 chain C region | IGHG1_HUMAN | 36 kDa | P01857 | *Homo sapiens* |
| 23 | Heparin cofactor 2 | HEP2_HUMAN | 57 kDa | P05546 | *Homo sapiens* |
| 24 | Ig gamma-2 chain C region | IGHG2_HUMAN | 36 kDa | P01859 | *Homo sapiens* |
| 25 | Ig kappa chain C region | KAC_HUMAN | 12 kDa | P01834 | *Homo sapiens* |
| 26 | N-acetylmuramoyl-L-alanine amidase | PGRP2_HUMAN | 62 kDa | Q96PD5 | *Homo sapiens* |
| 27 | Alpha-2-HS-glycoprotein | FETUA_HUMAN | 39 kDa | P02765 | *Homo sapiens* |
| 28 | Kininogen-1 | KNG1_HUMAN | 72 kDa | P01042 | *Homo sapiens* |
| 29 | Zinc-alpha-2-glycoprotein | ZA2G_HUMAN | 34 kDa | P25311 | *Homo sapiens* |
| 30 | Thyroxine-binding globulin | THBG_HUMAN | 46 kDa | P05543 | *Homo sapiens* |
| 31 | Corticosteroid-binding globulin | CBG_HUMAN | 45 kDa | P08185 | *Homo sapiens* |
| 32 | Attractin | ATRN_HUMAN | 159 kDa | O75882 | *Homo sapiens* |
| 33 | Pregnancy zone protein | PZP_HUMAN | 164 kDa | P20742 | *Homo sapiens* |
| 34 | Alpha-2-antiplasmin | A2AP_HUMAN | 55 kDa | P08697 | *Homo sapiens* |
| 35 | Vitronectin | VTNC_HUMAN | 54 kDa | P04004 | *Homo sapiens* |
| 36 | Ig lambda chain C regions | LAC_HUMAN | 11 kDa | P01842 | *Homo sapiens* |
| 37 | Apolipoprotein A-II | APOA2_HUMAN | 11 kDa | P02652 | *Homo sapiens* |
| 38 | Apolipoprotein C-III | APOC3_HUMAN | 11 kDa | P02656 | *Homo sapiens* |
| 39 | Insulin-like growth factor-binding protein complex acid labile chain | ALS_HUMAN | 66 kDa | P35858 | *Homo sapiens* |
| 40 | Complement C3 | CO3_HUMAN | 187 kDa | P01024 | *Homo sapiens* |
| 41 | Complement C4-B | CO4B_HUMAN | 193 kDa | P0C0L5 | *Homo sapiens* |
| 42 | Serum paraoxonase/arylesterase 1 | PON1_HUMAN | 40 kDa | P27169 | *Homo sapiens* |
| 43 | Plasma retinol-binding protein | RETBP_HUMAN | 23 kDa | P02753 | *Homo sapiens* |
| 44 | Carboxypeptidase N subunit 2 | CPN2_HUMAN | 61 kDa | P22792 | *Homo sapiens* |
| 45 | Beta-2-glycoprotein 1 | APOH_HUMAN | 38 kDa | P02749 | *Homo sapiens* |
| 46 | Inter-alpha-trypsin inhibitor heavy chain H2 | ITIH2_HUMAN | 106 kDa | P19823 | *Homo sapiens* |
| 47 | Clusterin | CLUS_HUMAN | 52 kDa | P10909 | *Homo sapiens* |
| 48 | Protein AMBP | AMBP_HUMAN | 39 kDa | P02760 | *Homo sapiens* |
| 49 | Ig heavy chain V-III region BRO | HV305_HUMAN | 13 kDa | P01766 | *Homo sapiens* |
| 50 | Dynactin subunit 2 | DCTN2_HUMAN | 44 kDa | Q13561 | *Homo sapiens* |
| 51 | Inter-alpha-trypsin inhibitor heavy chain H1 | ITIH1_HUMAN | 101 kDa | P19827 | *Homo sapiens* |
| 52 | Complement C2 | CO2_HUMAN | 83 kDa | P06681 | *Homo sapiens* |
| 53 | Serum amyloid P-component | SAMP_HUMAN | 25 kDa | P02743 | *Homo sapiens* |
| 54 | Lamin-A/C | LMNA_HUMAN | 74 kDa | P02545 | *Homo sapiens* |
| 55 | Phosphatidylinositol-glycan-specific phospholipase D | PHLD1_HUMAN | 92 kDa | P80108 | *Homo sapiens* |
| 56 | Alpha-1-acid glycoprotein 1 | A1AG1_HUMAN | 24 kDa | P02763 | *Homo sapiens* |
| 57 | Pigment epithelium-derived factor | PEDF_HUMAN | 46 kDa | P36955 | *Homo sapiens* |
| 58 | Apolipoprotein C-I | APOC1_HUMAN | 9 kDa | P02654 | *Homo sapiens* |
| 59 | Transcription intermediary factor 1-beta | TIF1B_HUMAN | 89 kDa | Q13263 | *Homo sapiens* |
| 60 | Leucine-rich alpha-2-glycoprotein | A2GL_HUMAN | 38 kDa | P02750 | *Homo sapiens* |
| 61 | Lumican | LUM_HUMAN | 38 kDa | P51884 | *Homo sapiens* |
| 62 | Ig kappa chain V-III region SIE | KV302_HUMAN | 12 kDa | P01620 | *Homo sapiens* |
| 63 | Actin, cytoplasmic 1 | ACTB_HUMAN | 42 kDa | P60709 | *Homo sapiens* |
| 64 | Apolipoprotein E | APOE_HUMAN | 36 kDa | P02649 | *Homo sapiens* |
| 65 | Kallistatin | KAIN_HUMAN | 49 kDa | P29622 | *Homo sapiens* |
| 66 | Myosin-15 | MYH15_HUMAN | 225 kDa | Q9Y2K3 | *Homo sapiens* |
| 67 | Carboxypeptidase B2 | CBPB2_HUMAN | 48 kDa | Q96IY4 | *Homo sapiens* |
| 68 | Serum amyloid A-4 protein | SAA4_HUMAN | 15 kDa | P35542 | *Homo sapiens* |
| 69 | Cholinesterase | CHLE_HUMAN | 68 kDa | P06276 | *Homo sapiens* |
| 70 | Apolipoprotein D | APOD_HUMAN | 21 kDa | P05090 | *Homo sapiens* |
| 71 | Tubulin beta-2C chain | TBB2C_HUMAN | 50 kDa | P68371 | *Homo sapiens* |
| 72 | Haptoglobin-related protein | HPTR_HUMAN | 39 kDa | P00739 | *Homo sapiens* |
| 73 | Hemoglobin subunit delta | HBD_HUMAN | 16 kDa | P02042 | *Homo sapiens* |
| 74 | Ig kappa chain V-IV region Len | KV402_HUMAN | 13 kDa | P01625 | *Homo sapiens* |
| 75 | Ig alpha-2 chain C region | IGHA2_HUMAN | 37 kDa | P01877 | *Homo sapiens* |
| 76 | Proteoglycan 4 | PRG4_HUMAN | 151 kDa | Q92954 | *Homo sapiens* |
| 77 | Histone H2A type 1-D | H2A1D_HUMAN | 14 kDa | P20671 | *Homo sapiens* |
| 78 | Biotinidase | BTD_HUMAN | 61 kDa | P43251 | *Homo sapiens* |
| 79 | Carboxypeptidase N catalytic chain | CBPN_HUMAN | 52 kDa | P15169 | *Homo sapiens* |
| 80 | Plasma kallikrein | KLKB1_HUMAN | 71 kDa | P03952 | *Homo sapiens* |
| 81 | Ig kappa chain V-II region TEW | KV204_HUMAN | 12 kDa | P01617 | *Homo sapiens* |
| 82 | Apolipoprotein C-II | APOC2_HUMAN | 11 kDa | P02655 | *Homo sapiens* |
| 83 | DNA-dependent protein kinase catalytic subunit | PRKDC_HUMAN | 469 kDa | P78527 | *Homo sapiens* |
| 84 | Heterogeneous nuclear ribonucleoprotein U-like protein 1 | HNRL1_HUMAN | 96 kDa | Q9BUJ2 | *Homo sapiens* |

TABLE 1-continued

Proteins identified in spent media of human embryos.

| SEQ ID NO. | Protein Name | Entry Name | Protein Molecular Weight | Accession Number | Taxonomy |
|---|---|---|---|---|---|
| 85 | Apolipoprotein B-100 | APOB_HUMAN | 516 kDa | P04114 | *Homo sapiens* |
| 86 | Heterogeneous nuclear ribonucleoproteins A2/B1 | ROA2_HUMAN | 37 kDa | P22626 | *Homo sapiens* |
| 87 | Tubulin alpha-ubiquitous chain | TBAK_HUMAN | 50 kDa | P68363 | *Homo sapiens* |
| 88 | Gelsolin | GELS_HUMAN | 86 kDa | P06396 | *Homo sapiens* |
| 89 | Tetranectin | TETN_HUMAN | 23 kDa | P05452 | *Homo sapiens* |
| 90 | Alpha-1-acid glycoprotein 2 | A1AG2_HUMAN | 24 kDa | P19652 | *Homo sapiens* |
| 91 | Ig heavy chain V-III region GAL | HV320_HUMAN | 13 kDa | P01781 | *Homo sapiens* |
| 92 | IgGFc-binding protein | FCGBP_HUMAN | 572 kDa | Q9Y6R7 | *Homo sapiens* |
| 93 | Lactotransferrin | TRFL_HUMAN | 78 kDa | P02788 | *Homo sapiens* |
| 94 | Histone H4 | H4_HUMAN | 11 kDa | P62805 | *Homo sapiens* |
| 95 | Glutathione peroxidase 3 | GPX3_HUMAN | 26 kDa | P22352 | *Homo sapiens* |
| 96 | Histone H2B type 1-M | H2B1M_HUMAN | 14 kDa | Q99879 | *Homo sapiens* |
| 97 | Apolipoprotein M | APOM_HUMAN | 21 kDa | Q95445 | *Homo sapiens* |
| 98 | E3 SUMO-protein ligase RanBP2 | RBP2_HUMAN | 358 kDa | P49792 | *Homo sapiens* |
| 99 | Ig kappa chain V-I region EU | KV106_HUMAN | 12 kDa | P01598 | *Homo sapiens* |
| 100 | Ig kappa chain V-I region Lay | KV113_HUMAN | 12 kDa | P01605 | *Homo sapiens* |
| 101 | Dermcidin OS = *Homo sapiens* | DCD_HUMAN | 11 kDa | P81605 | *Homo sapiens* |
| 102 | Leucine-rich repeats and immunoglobulin-like domains protein 2 | LRIG2_HUMAN | 119 kDa | O94898 | *Homo sapiens* |
| 103 | Protein S100-A8 | S10A8_HUMAN | 11 kDa | P05109 | *Homo sapiens* |
| 104 | Glyceraldehyde-3-phosphate dehydrogenase | G3P_HUMAN | 36 kDa | P04406 | *Homo sapiens* |
| 105 | Myosin-9 | MYH9_HUMAN | 227 kDa | P35579 | *Homo sapiens* |
| 106 | Ig kappa chain V-III region VG (Fragment) | KV309_HUMAN | 13 kDa | P04433 | *Homo sapiens* |
| 107 | Monocyte differentiation antigen CD14 | CD14_HUMAN | 40 kDa | P08571 | *Homo sapiens* |
| 108 | Heterogeneous nuclear ribonucleoprotein H | HNRH1_HUMAN | 49 kDa | P31943 | *Homo sapiens* |
| 109 | ATP-dependent DNA helicase 2 subunit 1 | KU70_HUMAN | 70 kDa | P12956 | *Homo sapiens* |
| 110 | Protein TFG | TFG_HUMAN | 43 kDa | Q92734 | *Homo sapiens* |
| 111 | Coagulation factor XII | FA12_HUMAN | 68 kDa | P00748 | *Homo sapiens* |
| 112 | Filaggrin-2 | FILA2_HUMAN | 248 kDa | Q5D862 | *Homo sapiens* |
| 113 | Prothrombin | THRB_HUMAN | 70 kDa | P00734 | *Homo sapiens* |
| 114 | Sex hormone-binding globulin | SHBG_HUMAN | 44 kDa | P04278 | *Homo sapiens* |
| 115 | Heat shock cognate 71 kDa protein | HSP7C_HUMAN | 71 kDa | P11142 | *Homo sapiens* |
| 116 | Histidine-rich glycoprotein | HRG_HUMAN | 60 kDa | P04196 | *Homo sapiens* |
| 117 | Heterogeneous nuclear ribonucleoprotein A3 | ROA3_HUMAN | 40 kDa | P51991 | *Homo sapiens* |
| 118 | Ig kappa chain V-III region B6 | KV301_HUMAN | 12 kDa | P01619 | *Homo sapiens* |
| 119 | Testis-expressed sequence 15 protein | TEX15_HUMAN | 315 kDa | Q9BXT5 | *Homo sapiens* |
| 120 | Polyadenylate-binding protein 1 | PABP1_HUMAN | 71 kDa | P11940 | *Homo sapiens* |
| 121 | Lipopolysaccharide-binding protein | LBP_HUMAN | 53 kDa | P18428 | *Homo sapiens* |
| 122 | Lamina-associated polypeptide 2, isoform alpha | LAP2A_HUMAN | 75 kDa | P42166 | *Homo sapiens* |
| 123 | Desmoplakin | DESP_HUMAN | 332 kDa | P15924 | *Homo sapiens* |
| 124 | Protein S100-A9 | S10A9_HUMAN | 13 kDa | P06702 | *Homo sapiens* |
| 125 | Far upstream element-binding protein 2 | FUBP2_HUMAN | 73 kDa | Q92945 | *Homo sapiens* |
| 126 | Platelet glycoprotein Ib alpha chain | GP1BA_HUMAN | 69 kDa | P07359 | *Homo sapiens* |
| 127 | Zinc finger and SCAN domain-containing protein 29 | ZSC29_HUMAN | 97 kDa | Q8IWY8 | *Homo sapiens* |
| 128 | Heterogeneous nuclear ribonucleoprotein H3 | HNRH3_HUMAN | 37 kDa | P31942 | *Homo sapiens* |
| 129 | Histone H3.3 | H33_HUMAN | 15 kDa | P84243 | *Homo sapiens* |
| 130 | Stress-70 protein, mitochondrial | GRP75_HUMAN | 74 kDa | P38646 | *Homo sapiens* |
| 131 | Ig kappa chain V-I region AG | KV101_HUMAN | 12 kDa | P01593 | *Homo sapiens* |
| 132 | Elongation factor 1-alpha 1 | EF1A1_HUMAN | 50 kDa | P68104 | *Homo sapiens* |
| 133 | RNA-binding protein FUS | FUS_HUMAN | 53 kDa | P35637 | *Homo sapiens* |
| 134 | DNA repair and recombination protein RAD54B | RA54B_HUMAN | 103 kDa | Q9Y620 | *Homo sapiens* |
| 135 | Hornerin | HORN_HUMAN | 282 kDa | Q86YZ3 | *Homo sapiens* |
| 136 | Tubulin beta chain | TBB5_HUMAN | 50 kDa | P07437 | *Homo sapiens* |
| 137 | Heterogeneous nuclear ribonucleoproteins C1/C2 | HNRPC_HUMAN | 34 kDa | P07910 | *Homo sapiens* |
| 138 | RecQ-mediated genome instability protein 1 | RMI1_HUMAN | 70 kDa | Q9H9A7 | *Homo sapiens* |
| 139 | Desmocollin-1 | DSC1_HUMAN | 100 kDa | Q08554 | *Homo sapiens* |
| 140 | Xaa-Pro dipeptidase | PEPD_HUMAN | 55 kDa | P12955 | *Homo sapiens* |
| 141 | Junction plakoglobin | PLAK_HUMAN | 82 kDa | P14923 | *Homo sapiens* |

TABLE 1-continued

Proteins identified in spent media of human embryos.

| SEQ ID NO. | Protein Name | Entry Name | Protein Molecular Weight | Accession Number | Taxonomy |
|---|---|---|---|---|---|
| 142 | U3 small nucleolar RNA-associated protein 14 homolog C | UT14C_HUMAN | 87 kDa | Q5TAP6 | Homo sapiens |
| 143 | Obscurin | OBSCN_HUMAN | 868 kDa | Q5VST9 | Homo sapiens |
| 144 | Elongation factor Tu, mitochondrial | EFTU_HUMAN | 50 kDa | P49411 | Homo sapiens |
| 145 | Heterogeneous nuclear ribonucleoprotein F | HNRPF_HUMAN | 46 kDa | P52597 | Homo sapiens |
| 146 | Desmoglein-1 | DSG1_HUMAN | 114 kDa | Q02413 | Homo sapiens |
| 147 | Heterogeneous nuclear ribonucleoprotein A1 | ROA1_HUMAN | 39 kDa | P09651 | Homo sapiens |
| 148 | ELAV-like protein 1 | ELAV1_HUMAN | 36 kDa | Q15717 | Homo sapiens |
| 149 | Pyrroline-5-carboxylate reductase 1, mitochondrial | P5CR1_HUMAN | 33 kDa | P32322 | Homo sapiens |
| 150 | Ig lambda chain V-I region WAH | LV106_HUMAN | 12 kDa | P04208 | Homo sapiens |
| 151 | Zinc finger and BTB domain-containing protein 10 | ZBT10_HUMAN | 92 kDa | Q96DT7 | Homo sapiens |
| 152 | Cystatin-C | CYTC_HUMAN | 16 kDa | P01034 | Homo sapiens |
| 153 | Major vault protein | MVP_HUMAN | 99 kDa | Q14764 | Homo sapiens |
| 154 | Phosphatidylcholine-sterol acyltransferase | LCAT_HUMAN | 50 kDa | P04180 | Homo sapiens |
| 155 | Sulfhydryl oxidase 1 | QSCN6_HUMAN | 83 kDa | O00391 | Homo sapiens |
| 156 | Far upstream element-binding protein 3 | FUBP3_HUMAN | 62 kDa | Q96I24 | Homo sapiens |
| 157 | Ig delta chain C region | IGHD_HUMAN | 42 kDa | P01880 | Homo sapiens |
| 158 | Plasma serine protease inhibitor | IPSP_HUMAN | 46 kDa | P05154 | Homo sapiens |
| 159 | Heterogeneous nuclear ribonucleoprotein R | HNRPR_HUMAN | 71 kDa | O43390 | Homo sapiens |
| 160 | Hemoglobin subunit gamma-1 | HBG1_HUMAN (+1) | 16 kDa | P69891 | Homo sapiens |
| 161 | TAR DNA-binding protein 43 | TADBP_HUMAN | 45 kDa | Q13148 | Homo sapiens |
| 162 | Neural cell adhesion molecule L1-like protein | CHL1_HUMAN | 135 kDa | O00533 | Homo sapiens |
| 163 | Bifunctional polynucleotide phosphatase/kinase | PNKP_HUMAN | 57 kDa | Q96T60 | Homo sapiens |
| 164 | Fibrocystin | PKHD1_HUMAN | 447 kDa | Q8TCZ9 | Homo sapiens |
| 165 | Heterogeneous nuclear ribonucleoprotein A/B | ROAA_HUMAN | 36 kDa | Q99729 | Homo sapiens |
| 166 | Peroxiredoxin-1 | PRDX1_HUMAN | 22 kDa | Q06830 | Homo sapiens |
| 167 | 40S ribosomal protein S16 | RS16_HUMAN | 16 kDa | P62249 | Homo sapiens |
| 168 | Heat shock 70 kDa protein 1 | HSP71_HUMAN | 70 kDa | P08107 | Homo sapiens |
| 169 | 40S ribosomal protein S25 | RS25_HUMAN | 14 kDa | P62851 | Homo sapiens |
| 170 | Fetuin-B | FETUB_HUMAN | 42 kDa | Q9UGM5 | Homo sapiens |
| 171 | Transferrin receptor protein 1 | TFR1_HUMAN | 85 kDa | P02786 | Homo sapiens |
| 172 | Myelin basic protein | MBP_HUMAN | 33 kDa | P02686 | Homo sapiens |
| 173 | Aldo-keto reductase family 1 member Cl | AK1C1_HUMAN | 37 kDa | Q04828 | Homo sapiens |
| 174 | Uncharacterized protein C19orf21 | CS021_HUMAN | 75 kDa | Q8IV12 | Homo sapiens |
| 175 | TATA-binding protein-associated factor 2N | RBP56_HUMAN | 62 kDa | Q92804 | Homo sapiens |
| 176 | ATP-dependent DNA helicase 2 subunit 2 | KU86_HUMAN | 83 kDa | P13010 | Homo sapiens |
| 177 | Sulfide:quinone oxidoreductase, mitochondrial | SQRD_HUMAN | 50 kDa | Q9Y6N5 | Homo sapiens |
| 178 | Interleukin enhancer-binding factor 2 | ILF2_HUMAN | 43 kDa | Q12905 | Homo sapiens |
| 179 | Prostaglandin F2-alpha receptor | PF2R_HUMAN | 40 kDa | P43088 | Homo sapiens |
| 180 | Peptidase inhibitor 16 | PI16_HUMAN | 49 kDa | Q6UXB8 | Homo sapiens |
| 181 | Actin, alpha cardiac muscle 1 | ACTC_HUMAN | 42 kDa | P68032 | Homo sapiens |
| 182 | E3 SUMO-protein ligase RanBP2 | RBP2_HUMAN | 358 kDa | P49792 | Homo sapiens |
| 183 | Mitochondrial import inner membrane translocase subunit TIM50 | TIM50_HUMAN | 40 kDa | Q3ZCQ8 | Homo sapiens |
| 184 | Heterogeneous nuclear ribonucleoprotein DO | HNRPD_HUMAN | 38 kDa | Q14103 | Homo sapiens |
| 185 | Interleukin enhancer-binding factor 3 | ILF3_HUMAN | 95 kDa | Q12906 | Homo sapiens |
| 186 | Heterogeneous nuclear ribonucleoprotein G | HNRPG_HUMAN | 42 kDa | P38159 | Homo sapiens |
| 187 | 40S ribosomal protein S4, X isoform | RS4X_HUMAN | 30 kDa | P62701 | Homo sapiens |
| 188 | Caspase-14 | CASPE_HUMAN | 28 kDa | P31944 | Homo sapiens |
| 189 | Annexin A2 | ANXA2_HUMAN | 39 kDa | P07355 | Homo sapiens |
| 190 | Isocitrate dehydrogenase [NAD] subunit alpha, mitochondrial | IDH3A_HUMAN | 40 kDa | P50213 | Homo sapiens |
| 191 | Cysteine-rich secretory protein 3 | CRIS3_HUMAN | 28 kDa | P54108 | Homo sapiens |
| 192 | Myeloperoxidase | PERM_HUMAN | 84 kDa | P05164 | Homo sapiens |

TABLE 1-continued

Proteins identified in spent media of human embryos.

| SEQ ID NO. | Protein Name | Entry Name | Protein Molecular Weight | Accession Number | Taxonomy |
|---|---|---|---|---|---|
| 193 | Transformation/transcription domain-associated protein | TRRAP_HUMAN | 438 kDa | Q9Y4A5 | *Homo sapiens* |
| 194 | Isocitrate dehydrogenase [NAD] subunit beta, mitochondrial | IDH3B_HUMAN | 42 kDa | O43837 | *Homo sapiens* |
| 195 | Collagen alpha-2(V) chain | CO5A2_HUMAN | 145 kDa | P05997 | *Homo sapiens* |
| 196 | Baculoviral IAP repeat-containing protein 6 | BIRC6_HUMAN | 528 kDa | Q9NR09 | *Homo sapiens* |
| 197 | Bleomycin hydrolase | BLMH_HUMAN | 53 kDa | Q13867 | *Homo sapiens* |
| 198 | Poly(rC)-binding protein 1 | PCBP1_HUMAN | 37 kDa | Q15365 | *Homo sapiens* |
| 199 | Tubulin beta-3 chain | TBB3_HUMAN | 50 kDa | Q13509 | *Homo sapiens* |
| 200 | 60 kDa heat shock protein, mitochondrial | CH60_HUMAN | 61 kDa | P10809 | *Homo sapiens* |
| 201 | ATP synthase subunit beta, mitochondrial | ATPB_HUMAN | 57 kDa | P06576 | *Homo sapiens* |
| 202 | 40S ribosomal protein S18 | RS18_HUMAN | 18 kDa | P62269 | *Homo sapiens* |
| 203 | DnaJ homolog subfamily A member 1 | DNJA1_HUMAN | 45 kDa | P31689 | *Homo sapiens* |
| 204 | RNA-binding motif, single-stranded-interacting protein 1 | RBMS1_HUMAN | 45 kDa | P29558 | *Homo sapiens* |
| 205 | 40S ribosomal protein S19 | RS19_HUMAN | 16 kDa | P39019 | *Homo sapiens* |
| 206 | Tubulin alpha-1 chain | TBA1_HUMAN | 50 kDa | P68366 | *Homo sapiens* |
| 207 | Protein Hook homolog 1 | HOOK1_HUMAN | 85 kDa | Q9UJC3 | *Homo sapiens* |
| 208 | Brother of CDO | BOC_HUMAN | 121 kDa | Q9BWV1 | *Homo sapiens* |
| 209 | Signal recognition particle 54 kDa protein | SRP54_HUMAN | 56 kDa | P61011 | *Homo sapiens* |
| 210 | Trinucleotide repeat-containing 6B protein | TNC6B_HUMAN | 194 kDa | Q9UP09 | *Homo sapiens* |
| 211 | Aldehyde dehydrogenase, dimeric NADP-preferring | AL3A1_HUMAN | 50 kDa | P30838 | *Homo sapiens* |
| 212 | 40S ribosomal protein S3 | RS3_HUMAN | 27 kDa | P23396 | *Homo sapiens* |
| 213 | Fatty aldehyde dehydrogenase | AL3A2_HUMAN | 55 kDa | P51648 | *Homo sapiens* |
| 214 | Electron transfer flavoprotein subunit alpha, mitochondrial | ETFA_HUMAN | 35 kDa | P13804 | *Homo sapiens* |
| 215 | RNA-binding protein EWS | EWS_HUMAN | 68 kDa | Q01844 | *Homo sapiens* |
| 216 | Histone H2A.V | H2AV_HUMAN (+1) | 14 kDa | Q71UI9 | *Homo sapiens* |
| 217 | Heterogeneous nuclear ribonucleoprotein Q | HNRPQ_HUMAN | 70 kDa | O60506 | *Homo sapiens* |
| 218 | Pyrroline-5-carboxylate reductase | P5CR2_HUMAN | 34 kDa | Q96C36 | *Homo sapiens* |
| 219 | Prohibitin | PHB_HUMAN | 30 kDa | P35232 | *Homo sapiens* |
| 220 | RuvB-like 1 | RUVB1_HUMAN | 50 kDa | Q9Y265 | *Homo sapiens* |
| 221 | Protein-glutamine gamma-glutamyltransferase | TGM2_HUMAN | 77 kDa | P21980 | *Homo sapiens* |
| 222 | Ubiquitin-associated protein 2 | UBAP2_HUMAN | 117 kDa | O5T6F2 | *Homo sapiens* |
| 223 | Latent-transforming growth factor beta-binding protein 1 | LTB1L_HUMAN | 187 kDa | Q14766 | *Homo sapiens* |
| 224 | Thioredoxin domain-containing protein 2 | TXND2_HUMAN | 60 kDa | Q86VQ3 | *Homo sapiens* |
| 225 | Leucine-rich repeat-containing protein 17 | LRC17_HUMAN | 52 kDa | Q8N6Y2 | *Homo sapiens* |
| 226 | Protein FAM105B | F105B_HUMAN | 40 kDa | Q96BN8 | *Homo sapiens* |
| 227 | Myosin-Ia | MYO1A_HUMAN | 118 kDa | Q9UBC5 | *Homo sapiens* |
| 228 | Ras GTPase-activating-like protein IQGAP2 | IQGA2_HUMAN | 181 kDa | Q13576 | *Homo sapiens* |
| 229 | 26S proteasome non-ATPase regulatory subunit 1 | PSMD1_HUMAN | 102 kDa | Q99460 | *Homo sapiens* |
| 230 | Actin, alpha skeletal muscle | ACTS_HUMAN | 42 kDa | P68133 | *Homo sapiens* |
| 231 | Cleavage stimulation factor subunit 3 | CSTF3_HUMAN | 83 kDa | Q12996 | *Homo sapiens* |
| 232 | Clusterin | CLUS_HUMAN | 52 kDa | P10909 | *Homo sapiens* |
| 233 | Fibrocystin-L | PKHL1_HUMAN | 466 kDa | Q86W11 | *Homo sapiens* |
| 234 | InaD-like protein | INADL_HUMAN | 196 kDa | Q8NI35 | *Homo sapiens* |
| 235 | Keratin, type I cuticular Ha1 | K1H1_HUMAN | 47 kDa | Q15323 | *Homo sapiens* |
| 236 | Keratin, type I cuticular Ha2 | K1H2_HUMAN | 50 kDa | Q14532 | *Homo sapiens* |
| 237 | Keratin, type I cuticular Ha6 | K1H6_HUMAN | 52 kDa | O76013 | *Homo sapiens* |
| 238 | Keratin, type I cytoskeletal 10 | K1C10_HUMAN | 59 kDa | P13645 | *Homo sapiens* |
| 239 | Keratin, type I cytoskeletal 14 | K1C14_HUMAN | 52 kDa | P02533 | *Homo sapiens* |
| 240 | Keratin, type I cytoskeletal 16 | K1C16_HUMAN | 51 kDa | P08779 | *Homo sapiens* |
| 241 | Keratin, type I cytoskeletal 18 | K1C18_HUMAN | 48 kDa | P05783 | *Homo sapiens* |
| 242 | Keratin, type I cytoskeletal 19 | K1C19_HUMAN | 44 kDa | P08727 | *Homo sapiens* |
| 243 | Keratin, type I cytoskeletal 9 | K1C9_HUMAN | 62 kDa | P35527 | *Homo sapiens* |
| 244 | Keratin, type II cuticular Hb1 | KR181_HUMAN | 55 kDa | Q14533 | *Homo sapiens* |
| 245 | Keratin, type II cuticular Hb5 | KR185_HUMAN | 56 kDa | P78386 | *Homo sapiens* |
| 246 | Keratin, type II cytoskeletal 1 | K2C1_HUMAN | 66 kDa | P04264 | *Homo sapiens* |

TABLE 1-continued

Proteins identified in spent media of human embryos.

| SEQ ID NO. | Protein Name | Entry Name | Protein Molecular Weight | Accession Number | Taxonomy |
|---|---|---|---|---|---|
| 247 | Keratin, type II cytoskeletal 1b | K2C1B_HUMAN | 62 kDa | Q7Z794 | Homo sapiens |
| 248 | Keratin, type II cytoskeletal 2 epidermal | K22E_HUMAN | 65 kDa | P35908 | Homo sapiens |
| 249 | Keratin, type II cytoskeletal 4 | K2C4_HUMAN | 57 kDa | P19013 | Homo sapiens |
| 250 | Keratin, type II cytoskeletal 5 | K2C5_HUMAN | 62 kDa | P13647 | Homo sapiens |
| 251 | Keratin, type II cytoskeletal 6B | K2C6B_HUMAN | 60 kDa | P04259 | Homo sapiens |
| 252 | Keratin, type II cytoskeletal 7 | K2C7_HUMAN | 51 kDa | P08729 | Homo sapiens |
| 253 | Keratin, type II cytoskeletal 8 | K2C8_HUMAN | 54 kDa | P05787 | Homo sapiens |
| 254 | Lymphoid-restricted membrane protein | LRMP_HUMAN | 62 kDa | Q12912 | Homo sapiens |
| 255 | Myosin light chain 1, skeletal muscle isoform | MLE1_HUMAN | 21 kDa | P05976 | Homo sapiens |
| 256 | Myosin-2 | MYH2_HUMAN | 223 kDa | Q9UKX2 | Homo sapiens |
| 257 | Protein Shroom3 | SHRM3_HUMAN | 216 kDa | Q8TF72 | Homo sapiens |
| 258 | Ras-related GTP-binding protein A | RRAGA_HUMAN | 37 kDa | Q7L523 | Homo sapiens |
| 259 | Sushi, nidogen and EGF-like domain-containing protein 1 | SNED1_HUMAN | 152 kDa | Q8TER0 | Homo sapiens |
| 260 | Retinol-binding protein 4 | RET4_HUMAN | 23 kDa | P02753 | Homo sapiens |

TABLE 2

Proteins identified in spent media of human embryos.*

| SEQ ID NO. | Protein Name | Entry Name | Protein Molecular Weight | Accession Number | Day of Embryo Development | Nature of Viability Marker |
|---|---|---|---|---|---|---|
| 261 | 14-3-3 protein zeta/delta | 1433Z_HUMAN | 28 kDa | P63104 | D1 | |
| 262 | 6-phosphofructokinase, muscle type, isoform 1 | K6PF_HUMAN | 85 kDa | P08237 | D1 | |
| 263 | 6-phosphofructokinase, muscle type, isoform 1 | K6PF_HUMAN | 82 kDa | P08237-2 | D1 | |
| 264 | Adenylate kinase isoenzyme 1 | KAD1_HUMAN | 22 kDa | P00568 | D1 | |
| 265 | Alpha-actinin-2 | ACTN2_HUMAN | 104 kDa | P35609 | D1 | |
| 266 | Beta-enolase, isoform 1 | ENOB_HUMAN | 47 kDa | P13929 | D1 | |
| 267 | Beta-enolase, isoform 2 | ENOB_HUMAN | 44 kDa | P13929-2 | D1 | |
| 268 | Beta-enolase, isoform 3 | ENOB_HUMAN | 42 kDa | P13929-3 | D1 | |
| 269 | Creatine kinase M-type | KCRM_HUMAN | 43 kDa | P06732 | D1 | |
| 270 | Fructose-bisphosphate aldolase A | ALDOA_HUMAN | 39 kDa | P04075 | D1 | |
| 271 | Glycogen phosphorylase, muscle form | PYGM_HUMAN | 97 kDa | P11217 | D1 | |
| 272 | L-lactate dehydrogenase A chain | LDHA_HUMAN | 37 kDa | P00338 | D1 | |
| 273 | Myosin-1 | MYH1_HUMAN | 223 kDa | P12882 | D1 | |
| 274 | Myosin-2 | MYH2_HUMAN | 223 kDa | Q9UKX2 | D1 | |
| 275 | Myosin-3 | MYH3_HUMAN | 224 kDa | P11055 | D1 | |
| 276 | Myosin-4 | MYH4_HUMAN | 223 kDa | Q9Y623 | D1 | |
| 277 | Myosin-6 | MYH6_HUMAN | 224 kDa | P13533 | D1 | |
| 278 | Myosin-7 | MYH7_HUMAN | 223 kDa | P12883 | D1 | |
| 279 | Myosin-8 | MYH8_HUMAN | 223 kDa | P13535 | D1 | |
| 280 | Phosphoglucomutase-1, isoform 1 | PGM1_HUMAN | 61 kDa | P36871 | D1 | |
| 281 | Phosphoglucomutase-1, isoform 2 | PGM1_HUMAN | 64 kDa | P36871-2 | D1 | |
| 282 | Phosphoglycerate kinase 1 | PGK1_HUMAN | 45 kDa | P00558 | D1 | |
| 283 | Phosphoglycerate mutase 1 | PGAM1_HUMAN | 29 kDa | P18669 | D1 | |
| 284 | Pyruvate kinase isozyme M2 | KPYM_HUMAN | 58 kDa | P14618 | D1 | |
| 285 | Pyruvate kinase isozyme M1 | KPYM_HUMAN | 58 kDa | P14618-2 | D1 | |
| 286 | Sarcoplasmic/endoplasmic reticulum calcium ATPase 1, Isoform SERCA1B | AT2A1_HUMAN | 110 kDa | O14983 | D1 | |
| 287 | Sarcoplasmic/endoplasmic reticulum calcium ATPase 1, Isoform SERCA1A | AT2A1_HUMAN | 109 kDa | O14983-2 | D1 | |
| 288 | Sarcoplasmic/endoplasmic reticulum calcium ATPase 2, isoform 1 | AT2A2_HUMAN | 115 kDa | P16615 | D1 | |
| 289 | Sarcoplasmic/endoplasmic reticulum calcium ATPase 2, isoform 2 | AT2A2_HUMAN | 110 kDa | P16615-2 | D1 | |
| 290 | Sarcoplasmic/endoplasmic reticulum calcium ATPase 2, isoform 3 | AT2A2_HUMAN | 110 kDa | P16615-3 | D1 | |

TABLE 2-continued

Proteins identified in spent media of human embryos.*

| SEQID NO. | Protein Name | Entry Name | Protein Molecular Weight | Accession Number | Day of Embryo Development | Nature of Viability Marker |
|---|---|---|---|---|---|---|
| 291 | Sarcoplasmic/endoplasmic reticulum calcium ATPase 2, isoform 4 | AT2A2_HUMAN | 112 kDa | P16615-4 | D1 | |
| 292 | Sarcoplasmic/endoplasmic reticulum calcium ATPase 2, isoform 5 | AT2A2_HUMAN | 110 kDa | P16615-5 | D1 | |
| 293 | Triosephosphate isomerase, isoform 1 | TPIS_HUMAN | 27 kDa | P60174 | D1 | |
| 294 | Triosephosphate isomerase, isoform 2 | TPIS_HUMAN | 27 kDa | P60174-21 | D1 | |
| 295 | Tropomyosin alpha-1 chain, isoform 1 | TPM1_HUMAN | 33 kDa | P09493 | D1 | |
| 296 | Tropomyosin alpha-1 chain, isoform 2 | TPM1_HUMAN | 27 kDa | P09493-2 | D1 | |
| 297 | Tropomyosin alpha-1 chain, isoform 3 | TPM1_HUMAN | 33 kDa | P09493-3 | D1 | |
| 298 | Tropomyosin alpha-1 chain, isoform 4 | TPM1_HUMAN | 33 kDa | P09493-4 | D1 | |
| 299 | Tropomyosin alpha-1 chain, isoform 5 | TPM1_HUMAN | 28 kDa | P09493-6 | D1 | |
| 300 | Tropomyosin alpha-3 chain, isoform 1 | TPM3_HUMAN | 33 kDa | P06753 | D1 | |
| 301 | Tropomyosin alpha-3 chain, isoform 2 | TPM3_HUMAN | 29 kDa | P06753-2 | D1 | |
| 302 | Tropomyosin alpha-3 chain, isoform 3 | TPM3_HUMAN | 29 kDa | P06753-3 | D1 | |
| 303 | Collagen alpha-1(I) chain | CO1A1_HUMAN | 139 kDa | P02452 | D1/D3 | |
| 304 | Cystatin-A | CYTA_HUMAN | 11 kDa | P01040 | D1/D3 | |
| 305 | Filaggrin | FILA_HUMAN | 435 kDa | P20930 | D1/D3 | |
| 306 | Keratinocyte proline-rich protein | KPRP_HUMAN | 64 kDa | Q5T749 | D1/D3 | |
| 307 | Selenium-binding protein 1, isoform 1 | SBP1_HUMAN | 52 kDa | Q13228 | D3 | |
| 308 | Selenium-binding protein 1, isoform 2 | SBP1_HUMAN | 45 kDa | Q13228-2 | D3 | |
| 309 | Fatty acid-binding protein, epidermal | FABP5_HUMAN | 15 kDa | Q01469 | D1/D3/D5 | Increased with implantation Success |
| 310 | Galectin-7 | LEG7_HUMAN | 15 kDa | P47929 | D1/D3/D5 | Increased with implantation Success |
| 311 | Ubiquitin | UBIQ_HUMAN | X kDa | P02248 | D1/D3/D5 | |
| 312 | Calmodulin-like protein 5 | CALL5_HUMAN | 16 kDa | Q9NZT1 | D1/D3/D5 | Increased with implantation Success |
| 313 | 14-3-3 protein sigma | 1433S_HUMAN | 28 kDa | P31947 | D1/D3/D5 | |
| 314 | Histone H2A type 1-A | H2A1A_HUMAN | 14 kDa | Q96QV6 | D1/D3/D5 | |
| 315 | Histone H3.1t | H31T_HUMAN | 16 kDa | Q16695 | D1/D3/D5 | |
| 316 | Histone H1.3 | H13_HUMAN | 22 kDa | P16402 | D3/D5 | Increased with Aneuploidy |
| 317 | Lysozyme C | LYSC_HUMAN | 17 kDa | P61626 | D3/D5 | Increased with implantation Success |
| 318 | Plakophilin-1, isoform 2 | PKP1_HUMAN | 83 kDa | Q13835 | D3/D5 | Increased with implantation Success |
| 319 | Plakophilin-1, isoform 1 | PKP1_HUMAN | 80 kDa | Q13835-2 | D3/D5 | |
| 320 | Abhydrolase domain-containing protein 12B, isoform 1 | AB12B_HUMAN | 41 kDa | Q7Z5M8 | D3/D5 | |
| 321 | Abhydrolase domain-containing protein 12B, isoform 2 | AB12B_HUMAN | 32 kDa | Q7Z5M8-2 | D3/D5 | |
| 322 | Abhydrolase domain-containing protein 12B, isoform 3 | AB12B_HUMAN | 29 kDa | Q7Z5M8-3 | D3/D5 | |
| 323 | Abhydrolase domain-containing protein 12B, isoform 4 | AB12B_HUMAN | 13 kDa | Q7Z5M8-4 | D3/D5 | |
| 324 | Abhydrolase domain-containing protein 12B, isoform 5 | AB12B_HUMAN | 25 kDa | Q7Z5M8-5 | D3/D5 | |
| 325 | 40S ribosomal protein SA | RSSA_HUMAN | 33 kDa | P08865 | D5 | |
| 326 | Arginase-1, isoform 1 | ARGI1_HUMAN | 35 kDa | P05089 | D5 | |
| 327 | Arginase-1, isoform 2 | ARGI1_HUMAN | 36 kDa | P05089-2 | D5 | |
| 328 | Arginase-1, isoform 3 | ARGI1_HUMAN | 25 kDa | P05089-3 | D5 | |
| 329 | Beta-2-microglobulin | B2MG_HUMAN | 14 kDa | P61769 | D5 | |

TABLE 2-continued

Proteins identified in spent media of human embryos.*

| SEQID NO. | Protein Name | Entry Name | Protein Molecular Weight | Accession Number | Day of Embryo Development | Nature of Viability Marker |
|---|---|---|---|---|---|---|
| 330 | Carbonic anhydrase 2 | CAH2_HUMAN | 29 kDa | P00918 | D5 | |
| 331 | Carboxypeptidase A4 | CBPA4_HUMAN | 47 kDa | Q9UI42 | D5 | |
| 332 | Catalase | CATA_HUMAN | 60 kDa | P04040 | D5 | |
| 333 | Cathepsin D | CATD_HUMAN | 45 kDa | P07339 | D5 | Increased with implantation Success |
| 334 | CD44 antigen, isoform 1 | CD44_HUMAN | 81 kDa | P16070 | D5 | Increased with implantation Success |
| 335 | CD44 antigen, isoform 2 | CD44_HUMAN | 3 kDa | P16070-2 | D5 | Increased with implantation Success |
| 336 | CD44 antigen, isoform 3 | CD44_HUMAN | 78 kDa | P16070-3 | D5 | Increased with implantation Success |
| 337 | CD44 antigen, isoform 4 | CD44_HUMAN | 77 kDa | P16070-4 | D5 | Increased with implantation Success |
| 338 | CD44 antigen, isoform 5 | CD44_HUMAN | 81 kDa | P16070-5 | D5 | Increased with implantation Success |
| 339 | CD44 antigen, isoform 6 | CD44_HUMAN | 77 kDa | P16070-6 | D5 | Increased with implantation Success |
| 340 | CD44 antigen, isoform 7 | CD44_HUMAN | 78 kDa | P16070-7 | D5 | Increased with implantation Success |
| 341 | CD44 antigen, isoform 8 | CD44_HUMAN | 74 kDa | P16070-8 | D5 | Increased with implantation Success |
| 342 | CD44 antigen, isoform 9 | CD44_HUMAN | 74 kDa | P16070-9 | D5 | Increased with implantation Success |
| 343 | CD44 antigen, isoform 10 | CD44_HUMAN | 53 kDa | P16070-10 | D5 | Increased with implantation Success |
| 344 | CD44 antigen, isoform 11 | CD44_HUMAN | 47 kDa | P16070-11 | D5 | Increased with implantation Success |
| 345 | CD44 antigen, isoform 12 | CD44_HUMAN | 39 kDa | P16070-12 | D5 | Increased with implantation Success |
| 346 | CD44 antigen, isoform 13 | CD44_HUMAN | 46 kDa | P16070-13 | D5 | Increased with implantation Success |
| 347 | CD44 antigen, isoform 14 | CD44_HUMAN | 43 kDa | P16070-14 | D5 | Increased with implantation Success |
| 348 | CD44 antigen, isoform 15 | CD44_HUMAN | 32 kDa | P16070-15 | D5 | Increased with implantation Success |
| 349 | CD44 antigen, isoform 16 | CD44_HUMAN | 73 kDa | P16070-16 | D5 | Increased with implantation Success |
| 350 | CD44 antigen, isoform 17 | CD44_HUMAN | 76 kDa | P16070-17 | D5 | Success |
| 351 | Creatine kinase B-type | KCRB_HUMAN | 43 kDa | P12277 | D5 | |
| 352 | Dermokine, isoform 1 | DMKN_HUMAN | 47 kDa | Q6E0U4 | D5 | |
| 353 | Dermokine, isoform 2 | DMKN_HUMAN | 47 kDa | Q6E0U4-2 | D5 | |

TABLE 2-continued

Proteins identified in spent media of human embryos.*

| SEQID NO. | Protein Name | Entry Name | Protein Molecular Weight | Accession Number | Day of Embryo Development | Nature of Viability Marker |
|---|---|---|---|---|---|---|
| 354 | Dermokine, isoform 3 | DMKN_HUMAN | 37 kDa | Q6E0U4-3 | D5 | |
| 355 | Dermokine, isoform 4 | DMKN_HUMAN | 45 kDa | Q6E0U4-4 | D5 | |
| 356 | Dermokine, isoform 5 | DMKN_HUMAN | 38 kDa | Q6E0U4-5 | D5 | |
| 357 | Dermokine, isoform 6 | DMKN_HUMAN | 42 kDa | Q6E0U4-6 | D5 | |
| 358 | Dermokine, isoform 7 | DMKN_HUMAN | 35 kDa | Q6E0U4-7 | D5 | |
| 359 | Dermokine, isoform 8 | DMKN_HUMAN | 20 kDa | Q6E0U4-8 | D5 | |
| 360 | Dermokine, isoform 9 | DMKN_HUMAN | 19 kDa | Q6E0U4-9 | D5 | |
| 361 | Dermokine, isoform 10 | DMKN_HUMAN | 17 kDa | Q6E0U4-10 | D5 | |
| 362 | Dermokine, isoform 11 | DMKN_HUMAN | 15 kDa | Q6E0U4-11 | D5 | |
| 363 | Dermokine, isoform 12 | DMKN_HUMAN | 16 kDa | Q6E0U4-12 | D5 | |
| 364 | Dermokine, isoform 13 | DMKN_HUMAN | 14 kDa | Q6E0U4-13 | D5 | |
| 365 | Dermokine, isoform 14 | DMKN_HUMAN | 15 kDa | Q6E0U4-14 | D5 | |
| 366 | Dermokine, isoform 15 | DMKN_HUMAN | 10 kDa | Q6E0U4-15 | D5 | |
| 367 | Extracellular glycoprotein lacritin | LACRT_HUMAN | 14 kDa | Q9GZZ8 | D5 | Increased with implantation Success |
| 368 | Ferritin light chain (Ferritin L subunit) | FRIL_HUMAN | 20 kDa | P02792 | D5 | |
| 369 | Fibrinogen gamma chain, isoform gamma-B | FIBG_HUMAN | 52 kDa | P02679 | D5 | |
| 370 | Fibrinogen gamma chain, isoform gamma-A | FIBG_HUMAN | 49 kDa | P02679-2 | D5 | Increased with implantation Success |
| 371 | Gamma-enolase | ENOG_HUMAN | 47 kDa | P09104 | D5 | |
| 372 | Gamma-glutamylcyclotransferase, isoform 1 | GGCT_HUMAN | 21 kDa | O75223 | D5 | |
| 373 | Gamma-glutamylcyclotransferase, isoform 2 | GGCT_HUMAN | 13 kDa | O75223-2 | D5 | Increased with implantation Success |
| 374 | Heat shock protein beta-1 | HSPB1_HUMAN | 23 kDa | P04792 | D5 | |
| 375 | Histidine ammonia-lyase | HUTH_HUMAN | 73 kDa | P42357 | D5 | |
| 376 | Ig mu chain C region, isoform 1 | IGHM_HUMAN | 49 kDa | P01871 | D5 | |
| 377 | Ig mu chain C region, isoform 2 | IGHM_HUMAN | 52 kDa | P01871-2 | D5 | |
| 378 | Interleukin-1 family member 7 precursor, isoform B | IL1F7_HUMAN | 224 kDa | Q9NZH6 | D5 | |
| 379 | Interleukin-1 family member 7 precursor, isoform A | IL1F7_HUMAN | 22kDa | Q9NZH6-2 | D5 | |
| 380 | Interleukin-1 family member 7 precursor, isoform C | IL1F7_HUMAN | 20 kDa | Q9NZH6-2 | D5 | |
| 381 | Interleukin-1 family member 7 precursor, isoform D | IL1F7_HUMAN | 22 kDa | Q9NZH6-2 | D5 | |
| 382 | Interleukin-1 family member 7 precursor, isoform E | IL1F7_HUMAN | 17 kDa | Q9NZH6-2 | D5 | Increased with Aneuploidy |
| 383 | Lipocalin-1 | LCN1_HUMAN | 19 kDa | P31025 | D5 | |
| 384 | Methionine synthase | METH_HUMAN | 141 kDa | O99707 | D5 | |
| 385 | Peroxiredoxin-2 | PRDX2_HUMAN | 22 kDa | P32119 | D5 | |
| 386 | Proprotein convertase subtilisin/kexin type 9, isoform 1 | PCSK9_HUMAN | 74 kDa | Q8NBP7 | D5 | |
| 387 | Proprotein convertase subtilisin/kexin type 9, isoform 2 | PCSK9_HUMAN | 21 kDa | Q8NBP7-2 | D5 | |
| 388 | Protein POF1B, isoform 1 | POF1B_HUMAN | 69 kDa | Q8WVV4 | D5 | |
| 389 | Protein POF1B, isoform 2 | POF1B_HUMAN | 68 kDa | Q8WVV4-2 | D5 | |
| 390 | Protein POF1B, isoform 3 | POF1B_HUMAN | 35 kDa | Q8WVV4-3 | D5 | Increased with implantation Success |
| 391 | Protein S100-A7 | S10A7_HUMAN | 11 kDa | P31151 | D5 | |
| 392 | Protein-glutamine gamma-glutamyltransferase E | TGM3_HUMAN | 77 kDa | Q08188 | D5 | |
| 393 | Pyruvate kinase isozymes M1/M2, isoform M2 | KPYM_HUMAN | 58 kDa | P14618 | D5 | |
| 394 | Pyruvate kinase isozymes M1/M2, isoform M1 | KPYM_HUMAN | 58 kDa | P14618-2 | D5 | |
| 395 | Receptor-type tyrosine-protein phosphatase gamma, isoform 1 | PTPRG_HUMAN | 162 kDa | P23470 | D5 | |
| 396 | Receptor-type tyrosine-protein phosphatase gamma, isoform 2 | PTPRG_HUMAN | 159 kDa | P23470-2 | D5 | Increased with implantation |

TABLE 2-continued

Proteins identified in spent media of human embryos.*

| SEQID NO. | Protein Name | Entry Name | Protein Molecular Weight | Accession Number | Day of Embryo Development | Nature of Viability Marker |
|---|---|---|---|---|---|---|
| 397 | Serine protease inhibitor Kazal-type 5, isoform f1 | ISK5_HUMAN | 121 kDa | Q9NQ38 | D5 | Success Increased with implantation |
| 398 | Serine protease inhibitor Kazal-type 5, isoform short | ISK5_HUMAN | 104 kDa | Q9NQ38 | D5 | Success Increased with implantation |
| 399 | Serine protease inhibitor Kazal-type 5, isoform long | ISK5_HUMAN | 124 kDa | Q9NQ38 | D5 | Success |
| 400 | Serpin B3, isoform 1 | SPB3_HUMAN | 45 kDa | P29508 | D5 | |
| 401 | Serpin B3, isoform 2 | SPB3_HUMAN | 39 kDa | P29508-2 | D5 | Increased with implantation |
| 402 | Uteroglobin | UTER_HUMAN | 10 kDa | P11684 | D5 | Success Increased with implantation |
| 403 | V-set and immunoglobulin domain-containing protein 8, isoform 1 | VSIG8_HUMAN | 44 kDa | Q5VU13 | D5 | Success Increased with implantation |
| 404 | V-set and immunoglobulin domain-containing protein 8, isoform 1 | VSIG8_HUMAN | 25 kDa | | D5 | Success |

*All Proteins are from *Homo Sapiens*

Example 2

Secretome Profiling to Predict Implantation Potential of a Human Embryo

The following nonlimiting example teaches by way of illustration, not by limitation, the fabrication and employment of a customized immunoassay test kit for secretome profiling of a human embryo Immunoassay test kit fabrication occurs by modifying the well surfaces of a 96-well microtiter plate. Each separate well of the microtiter plate is incubated with an unlabelled capture antibody that recognizes one specific protein from the secretome panel. Custom capture antibodies are purchased from Rockland Immunochemicals, Inc. After incubation for 12 hours at 4° C., capture antibodies passively adsorb to the well surface. Subsequently, all wells of the 96-well plate are washed three times with a buffer comprising 1× phosphate buffer saline and 0.1% Tween-20 (PBST), blocked with 1% bovine serum albumin (BSA) for 1 hour at ambient temperature and washed three times with PBST.

Human cleavage-stage embryos are cultured in 10 μL drops of G1 supplemented with 2.5 mg/mL recombinant albumin under oil at 37° C., 6% $CO_2$, 5% $O_2$ for 24 hours. The embryos are washed twice in G2 culture media and further cultured in 10 μL drops of G2 supplemented with 2.5 mg/mL recombinant albumin under oil at 37° C., 6% $CO_2$, 5% $O_2$ for 48 hours with a fresh drop of G2 media added after 24 hours. Spent media samples of blastocysts are transferred into 0.65 mL Eppendorf tubes. Control groups comprise media cultured and collected under the same conditions but without embryos.

Secretome profiling proceeds using spent media culture in a sandwich ELISA format. The spent media culture is diluted into phosphate buffer saline (PBS) buffer and further distributed to separate wells of said customized microtiter plate. After incubation for one hour at room temperature, the samples are aspirated and all wells are washed four times with PBST buffer. Primary antibodies, each recognizing a distinct protein from the secretome panel, are distributed into wells that correspond to appropriate capture antibodies and permitted to incubate for one hour at room temperature. The wells are washed four times with PBST and incubated with a secondary antibody conjugated with an enzyme. The term "secondary antibody" refers to an antibody that binds to primary antibodies and may be conjugated with detection probes such as enzymes or fluorophores. In one embodiment, the secondary antibody contains the horseradish peroxidase (HRP) enzyme that converts the chromogenic substrate, 3,3',5,5'-tetramethylbenzidene (TMB), into a blue product quantified at 655 nm on a spectrophotometer. In another embodiment, the HRP enzymatic reaction is stopped with a solution containing sulfuric acid and quantified at 450 nm.

In one embodiment, secretome profiling of a secretome panel of 261 individual proteins (Table 1), each selected for significant developmental competence and implantation potential, are monitored using said ELISA immunoassay test kit. In another embodiment, secretome profiling of a secretome panel comprising 37 proteins (Table 2) are monitored using said ELISA immunoassay test kit. Secretome profiling of the 37 individual proteins (Table 2) from spent media of human embryos correlates with embryonic viability and euploidy.

Changes may be made in the above methods and systems without departing from the scope hereof. It should be noted that the matter contained in the above description or shown in the accompanying drawings should be interpreted as illustrative and not in a limiting sense. The following claims are intended to cover all generic and specific features described herein, as well as all statements of the scope of the present method and system and reasonable variations thereof, which, as a matter of language, might be said to fall therebetween.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09874572B2). An electronic copy of the "Sequence Listing" will also be available from the USPTO upon request and payment of the fee set forth in 37 CFR 1.19(b)(3).

What is claimed is:

1. A method of predicting implantation success of a candidate embryo comprising:
   contacting embryo secretions in a culture media with an immunosorbent assay kit that comprises a solid-state substrate functionalized with at least two distinct capture proteins, wherein the first capture protein specifically binds a protein having an amino acid sequence of SEQ ID NO: 310, and wherein the one or more additional capture proteins specifically bind a protein having an amino acid sequence selected from the group consisting of SEQ ID NOs. 1-309 and 311-404, and
   determining the secretome profile of a candidate embryo to ascertain the absence or presence of proteins implicated in implantation success;
   wherein the presence of proteins implicated in implantation success predicts candidate embryo viability for implantation.

2. The method of claim 1, wherein the one or more additional capture proteins specifically bind a protein having an amino acid sequence selected from the group consisting of SEQ ID Nos. 261-309 and 311-404.

3. The method of claim 1, wherein the one or more additional capture proteins specifically bind a protein having an amino acid sequence selected from the group consisting of SEQ ID Nos. 311, 313, 317, 318, 319, 334, 335, 336, 337, 338, 339, 340, 341, 342, 343, 345, 346, 347, 348, 349, 350, 368, 371, 374, 383, 391, 397, 398, 399, 402, 403, and 404.

4. The method of claim 1, wherein the one or more additional capture proteins specifically bind a protein having an amino acid sequence selected from the group consisting of SEQ ID Nos. 311, 313, 318, 319, 334, 335, 336, 337, 338, 339, 340, 341, 342, 343, 345, 346, 347, 348, 349, 350, 368, 371, 374, 391, 397, 398, 399, 402, 403, and 404.

5. The method of claim 1, wherein the one or more additional capture proteins specifically bind a protein having an amino acid sequence selected from the group consisting of SEQ ID Nos. 317 and 383.

* * * * *

UNITED STATES PATENT AND TRADEMARK OFFICE
CERTIFICATE OF CORRECTION

PATENT NO.        : 9,874,572 B2
APPLICATION NO.   : 15/648296
DATED             : January 23, 2018
INVENTOR(S)       : William B. Schoolcraft, Mandy Katz-Jaffe and Susanna McReynolds It is certified that error appears in the above-identified patent and that said Letters Patent is hereby corrected as shown below:

Column 5, Line 41:
"chanced"
Should be:
--chances--

Column 5, Line 48:
"form"
Should be:
--from--

Signed and Sealed this
Twenty-ninth Day of May, 2018

Andrei Iancu
*Director of the United States Patent and Trademark Office*